United States Patent
Yin et al.

(10) Patent No.: US 12,121,236 B2
(45) Date of Patent: Oct. 22, 2024

(54) ELECTRIC SURGICAL STAPLER WITH STATE DISPLAY

(71) Applicant: SURGERY (SHENZHEN) MEDICAL TECHNOLOGY CO., LTD, Shenzhen (CN)

(72) Inventors: Hongyi Yin, Beijing (CN); Xianliang Zhou, Shaoyang (CN); Minhua Zheng, Shanghai (CN); Ming Qiu, Shanghai (CN); Xingang Zhang, Cangzhou (CN); Shuangmei Guo, Shuozhou (CN)

(73) Assignee: SURGERY (SHENZHEN) MEDICAL TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/670,804

(22) Filed: May 22, 2024

(65) Prior Publication Data
US 2024/0307064 A1    Sep. 19, 2024

Related U.S. Application Data

(63) Continuation of application No. PCT/CN2023/082275, filed on Mar. 17, 2023.

(30) Foreign Application Priority Data

Aug. 25, 2022 (CN) .......................... 202222255546.4

(51) Int. Cl.
*A61B 17/072* (2006.01)
*A61B 17/068* (2006.01)
(Continued)

(52) U.S. Cl.
CPC .......... *A61B 17/115* (2013.01); *A61B 17/068* (2013.01); *A61B 17/072* (2013.01);
(Continued)

(58) Field of Classification Search
CPC ................ A61B 17/068; A61B 17/072; A61B 17/07207; A61B 17/115;
(Continued)

(56) References Cited

U.S. PATENT DOCUMENTS 5,383,880 A * 1/1995 Hooven ............... A61B 17/072
606/213
5,609,560 A * 3/1997 Ichikawa ........... G05B 19/0421
600/101
(Continued)

FOREIGN PATENT DOCUMENTS

CN    1401736 A    4/2009
CN    109350155 A    2/2019
(Continued)

*Primary Examiner* — Scott A Smith
(74) *Attorney, Agent, or Firm* — Birchwood IP

(57) ABSTRACT

An electric surgical stapler with state display is provided, which includes a housing, an anastomosis bobbin, a jaw, a dynamic structure, a power supply structure, a control board, a state display screen, and an RF antenna. The dynamic structure, power supply structure, state display screen, and RF antenna are respectively electrically connected with the control board; the housing includes a display slot, an antenna slot, and a board slot. The state display screen is provided in the display slot, the RF antenna is provided in the antenna slot, the control board is provided in the board slot. The state display screen and RF antenna are arranged in parallel. In working state, the dynamic structure is controlled to drive the jaw to perform by the control board, thereby completing closing, firing, retraction and other operations, the state display screen synchronously displays an operation state and progress of the jaw.

10 Claims, 2 Drawing Sheets

(51) Int. Cl.
*A61B 17/115* (2006.01)
*A61B 90/98* (2016.01)
*A61B 17/00* (2006.01)

(52) U.S. Cl.
CPC .... *A61B 90/98* (2016.02); *A61B 2017/00199* (2013.01); *A61B 2017/00477* (2013.01); *A61B 17/07207* (2013.01); *A61B 2017/07214* (2013.01)

(58) Field of Classification Search
CPC ........... A61B 2017/00477; A61B 2017/07214; A61B 2017/00199; A61B 90/90; A61B 90/98
USPC ..... 227/19, 175.1, 175.2, 176.1; 606/1, 139, 606/219
See application file for complete search history.

(56) References Cited

U.S. PATENT DOCUMENTS

| | | | | |
|---|---|---|---|---|
| 6,017,354 A * | 1/2000 | Culp | ............... | A61B 17/1626 604/22 |
| 6,611,793 B1 * | 8/2003 | Burnside | ............ | A61B 18/1206 702/183 |
| 7,241,270 B2 * | 7/2007 | Horzewski | ............... | A61N 7/00 601/2 |
| 9,629,629 B2 * | 4/2017 | Leimbach | ......... | A61B 17/07207 |
| 9,901,342 B2 * | 2/2018 | Shelton, IV | ........... | A61B 90/06 |
| 9,913,648 B2 * | 3/2018 | Shelton, IV | ......... | A61B 17/072 |
| 10,085,748 B2 * | 10/2018 | Morgan | ................ | A61B 17/072 |
| 2003/0073981 A1 * | 4/2003 | Whitman | ......... | A61B 17/07207 606/1 |
| 2006/0278680 A1 * | 12/2006 | Viola | .................... | A61B 17/068 227/176.1 |
| 2007/0102473 A1 * | 5/2007 | Shelton, IV | ..... | A61B 17/07207 227/175.1 |
| 2007/0125826 A1 * | 6/2007 | Shelton, IV | ..... | A61B 17/07207 227/176.1 |
| 2007/0175950 A1 * | 8/2007 | Shelton, IV | ..... | A61B 17/07207 227/176.1 |
| 2007/0278277 A1 * | 12/2007 | Wixey | ............... | A61B 17/0686 227/176.1 |
| 2008/0185419 A1 * | 8/2008 | Smith | .................. | A61B 17/115 227/179.1 |
| 2009/0090763 A1 * | 4/2009 | Zemlok | ............ | A61B 17/07207 227/175.2 |

FOREIGN PATENT DOCUMENTS

| | | |
|---|---|---|
| CN | 212699005 U | 3/2021 |
| CN | 113907823 A | 1/2022 |
| CN | 114072076 A | 2/2022 |
| CN | 216908046 U | 7/2022 |

* cited by examiner

ELECTRIC SURGICAL STAPLER WITH STATE DISPLAY

CROSS-REFERENCE TO RELATED APPLICATIONS

This application is a continuation of International Application No. PCT/CN2023/082275, filed on Mar. 17, 2023, which claims priority to Chinese Patent Application No. 202222255546.4, filed on Aug. 25, 2022, both of which are hereby incorporated by reference in their entireties.

TECHNICAL FIELD

The present disclosure relates to the field of electric surgical stapler technologies, and in particular, to an electric surgical stapler with state display.

BACKGROUND

Minimally invasive surgery is increasingly becoming a preferred choice for a surgical procedure, and a surgical stapler is an important guarantee for a success of the minimally invasive surgery.

At present, when using the surgical stapler, in order to allow a doctor to understand a state of the stapler during use, the stapler needs to be externally connected to an LCD display screen, which renders it inconvenient to use the surgical stapler and leads to complex surgical site wiring, rendering it inconvenient for the doctor to work.

Meanwhile, in order to enhance an applicability of an electric surgical stapler, radio frequency antennas are often used to obtain a matching parameter and improve the applicability.

In existing technologies, integrating RF antennas and visualization screens in the same area with the electric surgical stapler often leads to structural interference.

SUMMARY

The purpose of the present disclosure is to provide an electric surgical stapler with state display, aiming to solve problem of structural interference caused by an integration of RF antenna and visualization screen in the existing technology of the electric surgical stapler.

The present disclosure is implemented in the following way: an electric surgical stapler with state display, including: a housing, an anastomosis bobbin, a jaw, a dynamic structure, a power supply structure, a control board, a state display screen, and an RF antenna; where an inner end of the anastomosis bobbin is connected to the housing, an outer end of the anastomosis bobbin is horizontally extended in a direction away from the housing, the outer end of the anastomosis bobbin is configured to install the jaw, the dynamic structure, the power supply structure, the control board, the state display screen, and the RF antenna are respectively provided on the housing; the dynamic structure, the power supply structure, the state display screen, and the RF antenna are electrically connected to the control board;

the housing includes a display slot and a board slot, the state display screen is provided in the display slot, the control board is provided in the board slot and arranged in a top-down direction, the display slot and board slot are arranged correspondingly; the RF antenna includes an antenna body and a pin, a lower of the pin is connected and arranged in a conductive manner with the control board, an upper of the pin is connected with the antenna body, the pin is arranged in a conductive manner with the antenna body, the antenna body is arranged in a suspended manner through the pin, and the antenna body is arranged between the state display screen and the control board.

In an embodiment, the pin is integrally arranged with the antenna body, and the pin is inclined and extended in a direction away from the control board.

In an embodiment, the electric surgical stapler with state display further includes four fixed columns, which are arranged at four corresponding corners, a lower of each fixed column is connected to the control board, an upper of each fixed column extends vertically away from the control board; and the upper of each fixed column abuts against the RF antenna, the four fixed columns form a fixed area, and the antenna body is provided in the fixed area.

In an embodiment, the display slot includes a display side wall and a display bottom wall, the display side wall is configured to form an upper opening and a lower opening, the display bottom wall covers the lower opening, the display bottom wall is configured to support the state display screen, the display side wall is configured to clamp and fix the state display screen, and the display bottom wall has a hollow structure, the hollow structure is connected to an interior of the housing.

In an embodiment, a screen fastener is respectively provided on two sides of the state display screen, the screen fastener includes a screen fixing spring and a screen fixing block, an inner end of the screen fixing spring is fixedly arranged, an outer end of the screen fixing spring is connected with the screen fixing block, the screen fixing block includes a screen fixing surface, which is gradually inclined upwards along a direction away from the screen fixing spring; the screen fixing surface is compressed and moves in a direction facing the screen fixing spring; the display side wall is provided with a side wall groove, and the screen fixing block is embedded with the side wall groove.

In an embodiment, the state display screen includes a display surface, a spacing is formed between the screen fixing block and the display surface, a slot spacing is formed between the side wall groove and an upper surface of the housing, the spacing is arranged to be consistence with the slot spacing, and the display surface is arranged to be flush with the upper surface of the housing.

In an embodiment, the state display screen is an OLED screen or an LCD screen.

In an embodiment, the RF antenna is a RFID antenna, which is horizontally extended and arranged in a flat shape along a horizontal direction.

In an embodiment, the housing includes a main housing and a handle housing, the main housing and the handle housing are arranged in a connected manner, the handle housing is configured for a user to hold, the dynamic structure and the power supply structure are respectively provided in the handle housing, the control board, state display screen, and RF antenna are respectively provided in the main housing; the power supply structure includes a battery pack that is a storage battery, the battery pack is arranged for charging or discharging; or the power supply structure includes a DC power supply configured to conduct with an external DC power supply, and the DC power supply is provided with a communication line, which is electrically connected to the control board and configured to feedback signal to the control board.

In an embodiment, the jaw includes an identification slot, which is provided with a RFID tag, and the RFID tag stores specification and model of the jaw.

Compared with existing technologies, the electric surgical stapler with state display provided by the present disclosure, the power supply structure is configured for power supply, which enables the dynamic structure, control board, state display screen, and RF antenna to have electrical energy. An operation of the dynamic structure is controlled to operate by the control board to render the jaw to be in an initial position, and the state display screen prompts a loading of the jaw; in a formal work state, an instruction is outputted by an operator to the control board to control the dynamic structure to drive the operation of the jaw, thereby complete the closing, firing, retraction and other operations. At the same time, the state display screen synchronously displays an operation state and progress of the jaw; in this way, due to a parallel arrangement of the state display screen and the RF antenna, a structural interference between the state display screen and RF antenna is avoided, and a compatibility of the electric stapler between the state display and RF antenna is achieved, which is very practical.

DESCRIPTION OF EMBODIMENTS

Figure 1:
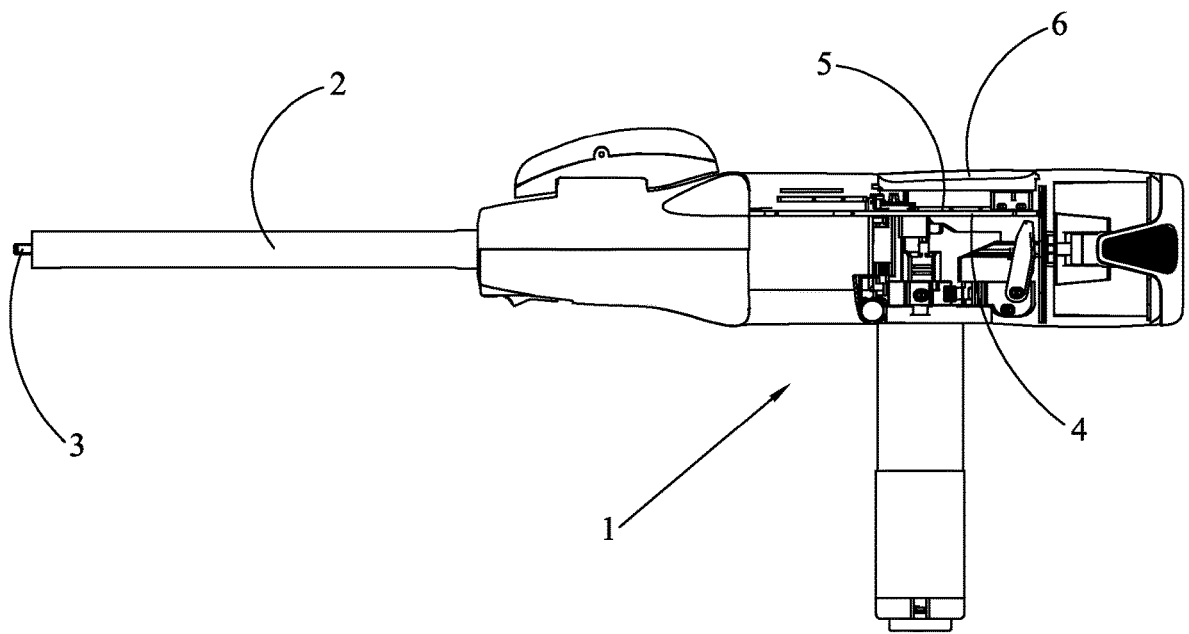
FIG. 1 is a sectional schematic diagram of an electric surgical stapler with state display provided by the present disclosure.

In order to make the purpose, technical solution, and advantages of the present disclosure clearer and understandable, the following is a further detailed explanation of the present disclosure in combination with the accompanying drawings and embodiments. It should be understood that the specific embodiments described here are only intended to explain the present disclosure and are not intended to limit the present disclosure.

The following provides a detailed description of the implementation of the present disclosure in combination with specific embodiments.

The same or similar symbols in the drawings of the embodiment correspond to the same or similar components; in the description of the present disclosure, it should be understood that if there are terms such as "up", "down", "left", "right" indicating an orientation or position relationship based on the orientation or position relationship shown in the drawings, it is only for a convenience of describing the present disclosure and simplifying the description, and not to indicate or imply that the device or component referred to must have a specific orientation, be constructed and operated in a specific orientation. Therefore, terms describing the position relationship in the drawings are only for illustrative purposes and cannot be understood as a limitation of the present disclosure. For ordinary technical personnel in this field, a specific meaning of the above terms can be understood according to a specific circumstance.

Figure 2:
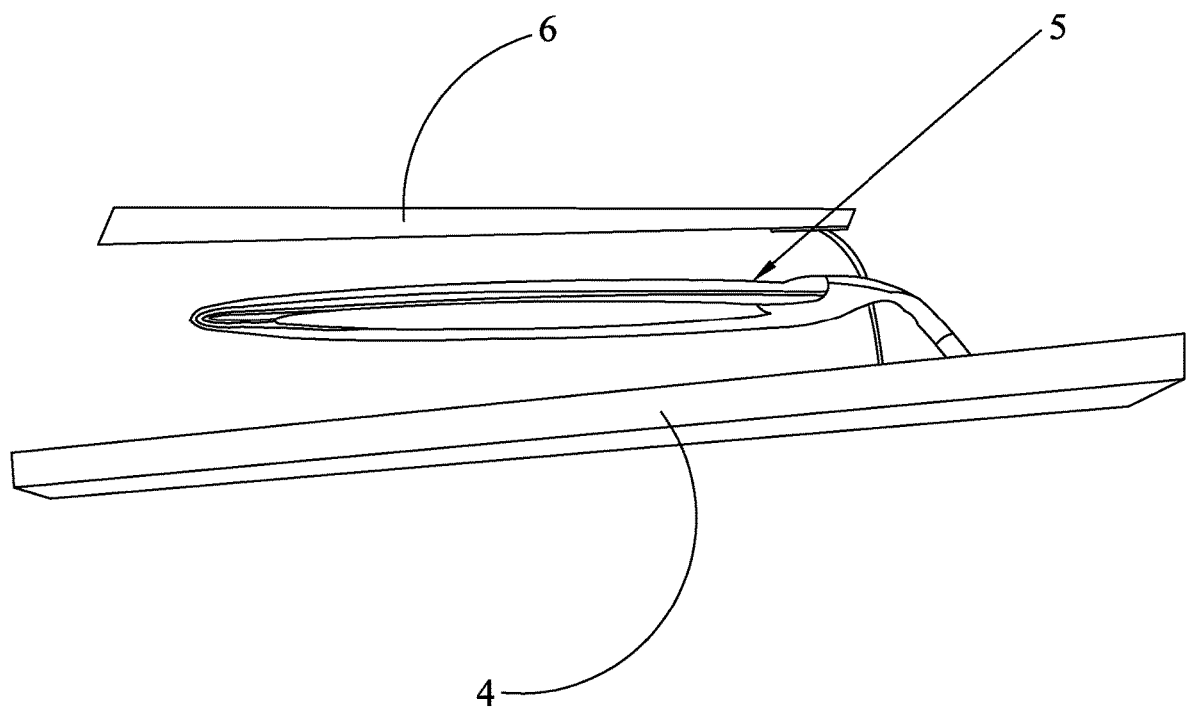
FIG. 2 is a schematic diagram of a layout of a control board, a state display screen, and RF antenna of the electric surgical stapler with state display provided by the present disclosure.

Referring to FIGS. 1-2, an embodiment is provided for the present disclosure.

An electric surgical stapler with state display includes a housing 1, an anastomosis bobbin 2, a jaw 3, a dynamic structure, a power supply structure, a control board 4, a state display screen 6, and an RF antenna 5. An inner end of the anastomosis bobbin 2 is connected to the housing 1, an outer end of the anastomosis bobbin 2 is horizontally extended in a direction away from the housing 1. The outer end of the anastomosis bobbin 2 is configured to install the jaw 3. The dynamic structure, power supply structure, control board 4, state display screen 6, and RF antenna 5 are respectively provided on the housing 1. The dynamic structure, power supply structure, state display screen 6, and RF antenna 5 are electrically connected to the control board 4.

The housing 1 includes a display slot and a board slot, the state display screen 6 is provided in the display slot, the control board 4 is provided in the board slot and arranged in a top-down direction. The display slot and board slot are arranged correspondingly. The RF antenna 6 includes an antenna body and a pin, a lower of the pin is connected and arranged in a conductive manner with the control board 4. An upper of the pin is connected with the antenna body, the pin is arranged in a conductive manner with the antenna body. The antenna body is arranged in a suspended manner through the pin, and the antenna body is arranged between the state display screen 6 and the control board 4.

The electric surgical stapler with state display has a power supply structure for power supply, which enables the dynamic structure, control board 4, state display screen 6, and RF antenna 5 to have electrical energy. The control board 4 controls an operation of the dynamic structure to render the jaw 3 at an initial position, and the state display screen 6 prompts a loading of the jaw 3; in a formal work state, an instruction is outputted by an operator to the control board 4 to drive an operation of the jaw 3 through the dynamic structure, thereby completing closing, firing, retraction, and other operations. At the same time, the state display screen 6 synchronously displays an operation state and progress of the jaw 3. In this way, due to a parallel arrangement of the state display screen 6 and RF antenna 5, a structural interference between the state display screen 6 and RF antenna 5 is avoided, and a compatibility of the electric stapler between the state display and RF antenna 5 is achieved, which is very practical.

The jaw 3 includes an identification slot, which is provided with a RFID tag. The RFID tag stores specifications and models of the jaw 3.

After loading the jaw 3, an instruction is outputted by the control board 4 to render the state display screen 6 to read the RFID tag. At the same time, the RFID antenna hidden below the state display screen 6 is activated by the control board 4. When the RFID tag is placed by the operator within 2 cm above the state display screen 6, the RFID tag information is captured by the control board 4 through the RFID antenna and it is processed to obtain a model parameter of the jaw 3.

The dynamic structure includes a first motor, a second motor, and a transmission. The first motor and the second motor are respectively electrically connected and arranged with the control board 4. The control board 4 is configured to control the first motor and the second motor to rotate forward or reverse. The transmission includes a closed transmission group and a firing transmission group. The closed transmission group is connected to the first motor, the closed transmission group is configured to complete a closing operation of the stapler, the firing transmission group is connected to the second motor, and the firing transmission group is configured to complete a firing operation of the stapler.

The pin is integrally arranged with the antenna body, which facilitates assembly and production of the RF antenna 5, and reduces a cost of the RF antenna 5.

The pin is inclined and extended in a direction away from the control board 4. In this way, the antenna body and control board 4 are arranged in parallel at intervals to avoid a mutual influence between the antenna body and control board 4, thereby ensuring a normal use of the antenna body.

The housing 1 is provided with a conducting column, which synchronously runs through the board slot and antenna slot. The conducting column is fixedly provided with the housing 1, a lower of the conducting column is connected and arranged in a conducting manner with control board 4, an upper of the conducting column is connected and arranged in a conducting manner with RF antenna 5; with the conducting column, a relative stability between the RF antenna 5 and the control board 4 is enhanced, while effectively ensuring that RF antenna 5 and control board 4 are arranged in a conductive manner.

The electric surgical stapler with state display includes four fixed columns which are arranged at four corresponding corners, a lower of each fixed column is connected to the control board 4. An upper of each fixed column extends vertically away from the control board 4, and the upper of each fixed column abuts against the RF antenna 5. The four fixed columns form a fixed area, and the antenna body is provided in the fixed area; under a coordination of four fixed columns, a relative stability between the RF antenna 5 and the control board 4 is enhanced, while effectively ensuring that RF antenna 5 and control board 4 are arranged in a conductive manner.

The display slot includes a display sidewall and a display bottom wall, the display side wall is configured to form an upper opening and a lower opening. The display bottom wall is configured to cover the lower opening, the display bottom wall is configured to support the state display screen 6. And the display side wall is configured to clamp and fix the state display screen 6, with a cooperation of the display bottom wall and the display side wall, an installation of the state display screen 6 is achieved.

A bottom of the display bottom wall includes a hollow structure, the hollow structure is arranged in a connected manner with an interior of the housing 1, thereby reducing heat accumulation during the use of the state display screen 6 and facilitating heat dissipation.

A screen fastener is respectively provided on two sides of the state display screen 6, the screen fastener includes a screen fixing spring and a screen fixing block. An inner end of the screen fixing spring is fixedly arranged, an outer end of the screen fixing spring is connected with the screen fixing block. The screen fixing block includes a screen fixing surface, which is gradually inclined upwards along a direction away from the screen fixing spring. The screen fixing surface is compressed and moves in a direction facing the screen fixing spring; the display side wall is provided with a side wall groove, and the screen fixing block is embedded with the side wall groove.

In this way, when installing the state display screen 6, the display slot of the state display screen 6 and the housing 1 are arranged in a corresponding manner. A squeezing force is applied to the state display screen 6 to render the state display screen 6 to move towards the display slot, a reaction force from the housing 1 is received by the screen fixing block, and the screen fixing block is caused to move and squeeze the screen fixing spring until the state display screen 6 moves to a position where the state display screen 6 is horizontally arranged with the side wall groove, the screen fixing spring is reset and causes the screen fixing block to be embedded in the side wall groove, thereby enhancing a stability of the installation of the state display screen 6.

The state display screen 6 includes a display surface, a spacing is formed between the screen fixing block and the display surface, a slot spacing is formed between the side wall groove and an upper surface of the housing 1, the spacing is arranged to be consistence with the slot spacing. The display surface is arranged to be flush with the upper surface of the housing 1. In this way, an installed state display screen 6 is arranged to be flush with an outer surface of the housing 1 to avoid affecting the user's operation.

The state display screen 6 is an OLED screen, the OLED screen has high brightness, high efficiency, wide viewing angle, autonomous luminescence, all solid state, ultra-thin and ultra-light, simple manufacturing process, fast response speed, can achieve full-color display, and good mechanical processing performance, and it can be made into display screens with different shapes.

In an implementation, the state display screen 6 is an LCD screen, which is constructed by placing a liquid crystal between two parallel pieces of glass. There are many small vertical and horizontal wires in a middle of the two pieces of glass, which control direction of rod-shaped crystal molecules by being electrified or not, light is refracted to produce a picture; the LCD screen has a longer lifespan, lower energy consumption, and lower cost.

The RF antenna 5 is an RFID antenna, which is horizontally extended and arranged in a flat shape along a horizontal direction; thereby reducing a space occupied by RFID antenna and facilitating an arrangement of the RFID antenna.

The housing 1 includes a main housing and a handle housing, the main housing and the handle housing are arranged in a connected manner. The handle housing is configured for a user to hold, and the dynamic structure and power supply structure are respectively provided in the handle housing. The control board 4, state display screen 6, and RF antenna 5 are respectively provided in the main housing; the power supply structure includes a battery pack, which is a storage battery, the battery pack is arranged for charging or discharging. In an implementation, the power supply structure includes a DC power supply, which is configured to conduct with an external DC power supply. The DC power supply is provided with a communication line, which is electrically connected to the control board 4 and configured to feedback signal to the control board 4.

The above is only a preferred embodiment of the present disclosure and is not intended to limit it. Any modifications, equivalent replacements, and improvements made within the spirit and principles of the present disclosure should be included within the protection scope of the present disclosure.

What is claimed is:

1. An electric surgical stapler with state display, comprising a housing, an anastomosis bobbin, a jaw, a dynamic structure, a power supply structure, a control board, a state display screen, and an RF antenna; wherein an inner end of the anastomosis bobbin is connected to the housing, an outer end of the anastomosis bobbin is horizontally extended in a direction away from the housing, the outer end of the anastomosis bobbin is configured to install the jaw, the dynamic structure, the power supply structure, the control board, the state display screen, and the RF antenna are respectively provided on the housing; the dynamic structure, the power supply structure, the state display screen, and the RF antenna are electrically connected to the control board;

the housing comprises a display slot and a board slot, the state display screen is provided in the display slot, the control board is provided in the board slot and arranged in a top-down direction, the display slot and board slot are arranged correspondingly; the RF antenna comprises an antenna body and a pin, a lower of the pin is connected and arranged in a conductive manner with the control board, an upper of the pin is connected with the antenna body, the pin is arranged in a conductive manner with the antenna body, the antenna body is arranged in a suspended manner through the pin, and the antenna body is arranged between the state display screen and the control board.

2. The electric surgical stapler with state display as claimed in claim 1, wherein the pin is integrally arranged with the antenna body, and the pin is inclined and extended in a direction away from the control board.

3. The electric surgical stapler with state display as claimed in claim 2, further comprising four fixed columns, which are arranged at four corresponding corners, a lower of each fixed column is connected to the control board, an upper of each fixed column extends vertically away from the control board; and the upper of each fixed column abuts against the RF antenna, the four fixed columns form a fixed area, and the antenna body is provided in the fixed area.

4. The electric surgical stapler with state display as claimed in claim 1, wherein the display slot comprises a display side wall and a display bottom wall, the display side wall is configured to form an upper opening and a lower opening, the display bottom wall covers the lower opening, the display bottom wall is configured to support the state display screen, the display side wall is configured to clamp and fix the state display screen, and the display bottom wall has a hollow structure, the hollow structure is connected to an interior of the housing.

5. The electric surgical stapler with state display as claimed in claim 4, wherein a screen fastener is respectively provided on two sides of the state display screen, the screen fastener comprises a screen fixing spring and a screen fixing block, an inner end of the screen fixing spring is fixedly arranged, an outer end of the screen fixing spring is connected with the screen fixing block, the screen fixing block comprises a screen fixing surface, which is gradually inclined upwards along a direction away from the screen fixing spring; the screen fixing surface is compressed and moves in a direction facing the screen fixing spring; the display side wall is provided with a side wall groove, and the screen fixing block is embedded with the side wall groove.

6. The electric surgical stapler with state display as claimed in claim 5, wherein the state display screen comprises a display surface, a spacing is formed between the screen fixing block and the display surface, a slot spacing is formed between the side wall groove and an upper surface of the housing, the spacing is arranged to be consistence with the slot spacing, and the display surface is arranged to be flush with the upper surface of the housing.

7. The electric surgical stapler with state display as claimed in claim 1, wherein the state display screen is an OLED screen or an LCD screen.

8. The electric surgical stapler with state display as claimed in claim 1, wherein the RF antenna is a RFID antenna, which is horizontally extended and arranged in a flat shape along a horizontal direction.

9. The electric surgical stapler with state display as claimed in claim 1, wherein the housing comprises a main housing and a handle housing, the main housing and the handle housing are arranged in a connected manner, the handle housing is configured for a user to hold, the dynamic structure and the power supply structure are respectively provided in the handle housing, the control board, state display screen, and RF antenna are respectively provided in the main housing; the power supply structure comprises a battery pack that is a storage battery, the battery pack is arranged for charging or discharging; or the power supply structure comprises a DC power supply configured to conduct with an external DC power supply, and the DC power supply is provided with a communication line, which is electrically connected to the control board and configured to feedback signal to the control board.

10. The electric surgical stapler with state display as claimed in claim 1, wherein the jaw comprises an identification slot, which is provided with a RFID tag, and the RFID tag stores specification and model of the jaw.

* * * * *